(12) United States Patent
Schaeffer-Korbylo et al.

(10) Patent No.: US 9,622,956 B2
(45) Date of Patent: Apr. 18, 2017

(54) ORAL CARE COMPOSITIONS

(75) Inventors: Lyndsay Schaeffer-Korbylo, Flemington, NJ (US); Jason Nesta, Cedar Knolls, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 135 days.

(21) Appl. No.: 14/366,944

(22) PCT Filed: Dec. 21, 2011

(86) PCT No.: PCT/US2011/066503
§ 371 (c)(1),
(2), (4) Date: Jun. 19, 2014

(87) PCT Pub. No.: WO2013/095439
PCT Pub. Date: Jun. 27, 2013

(65) Prior Publication Data
US 2014/0377192 A1    Dec. 25, 2014

(51) Int. Cl.
*A61K 8/66* (2006.01)
*A61Q 11/00* (2006.01)

(52) U.S. Cl.
CPC ............... *A61K 8/66* (2013.01); *A61Q 11/00* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 3,535,421 A | 10/1970 | Briner et al. |
| 3,538,230 A | 11/1970 | Pader et al. |
| 3,678,154 A | 7/1972 | Widder et al. |
| 3,862,307 A | 1/1975 | Di Giulio |
| 3,937,807 A | 2/1976 | Haefele |
| 3,959,458 A | 5/1976 | Agricola et al. |
| 4,051,234 A | 9/1977 | Gieske et al. |
| 4,335,101 A | 6/1982 | Stoudt et al. |
| 4,340,583 A | 7/1982 | Wason |
| 4,364,926 A | 12/1982 | Yokogawa et al. |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,188,821 A | 2/1993 | Gaffar et al. |
| 5,192,531 A | 3/1993 | Gaffar et al. |
| 6,692,726 B1 | 2/2004 | Morgan et al. |
| 7,354,569 B2 | 4/2008 | Du-Thumm et al. |
| 2003/0118572 A1 | 6/2003 | Deussen et al. |
| 2005/0058744 A1 | 3/2005 | Steinberg et al. |
| 2005/0239043 A1 | 10/2005 | Harding |
| 2008/0014224 A1* | 1/2008 | Boyd ................... A61K 8/0208 424/401 |
| 2009/0202450 A1* | 8/2009 | Prencipe ................. A61K 8/19 424/50 |
| 2011/0223117 A1 | 9/2011 | Kim et al. |

FOREIGN PATENT DOCUMENTS

| | | |
|---|---|---|
| CN | 1043740 | 5/1995 |
| EP | 0824019 | 2/1998 |
| FR | 2051992 | 4/1971 |
| JP | 3261703 | 3/2002 |
| JP | 4316512 | 8/2009 |
| RU | 2416391 | 4/2011 |
| WO | WO9920239 | 4/1999 |
| WO | WO2011072009 | 6/2011 |

OTHER PUBLICATIONS

Berg C.H. et al., "Proteolytic degradation of oral biofilms in vitro and in vivo: potential of proteases originating from Euphausia superba for plaque control", Eur J Oral Sci, 2008, 109(5):316-324.
Chinese Search Report issued in corresponding Chinese Patent Application No. 201180075717.7 on Apr. 30, 2015.
Lequette Y. et al., "Using enzymes to remove biofilms of bacterial isolates sampled in the food-industry", Biofouling, 2010, 26(4):421-431 (abstract only).
Leroy C. et al., "Effects of commercial enzymes on the adhesion of a marine biofilm-forming bacterium", Biofouling., 2008, 24(1):11-22.
International Search Report and the Written Opinion issued in International Application PCT/US2011/066503 mailed May 10, 2012.
Written Opinion of the International Preliminary Examining Authority issued in International Application PCT/US2011/066503 mailed Jan. 23, 2014.
Corresponding Official Action issued from the Patent Office of the Russian Federation on Feb. 24, 2016.

* cited by examiner

*Primary Examiner* — Nashaat Nashed
*Assistant Examiner* — William W Moore

(57) ABSTRACT

Described herein are oral care compositions comprising an effective amount of an enzyme cocktail, wherein the enzyme cocktail comprises an alkaline protease and a second enzyme selected from cellulose, α-glucanase, and combinations thereof, in an orally acceptable carrier, together with methods of making and using the same.

10 Claims, No Drawings

ORAL CARE COMPOSITIONS

BACKGROUND

Oral plaque consists of a wide variety of bacterial species embedded in a structural and functional matrix, called a biofilm. In addition to the bacteria, a variety of extracellular components are essential to the structure and function of this biofilm. Extracellular components of the plaque biofilm include: carbohydrates, nucleic acids, lipids, structural proteins, adhesins and signaling molecules. All of these components perform roles in maintaining structure of the biofilm or facilitating the transfer of signals and nutrients throughout the community. Traditional methods of oral cleaning have focused on the removal or killing of bacteria. Mechanical debridement through brushing and flossing removes all or part of the accumulated plaque. Chemical agents, such as cetylpyridinium chloride or triclosan usually focus on killing the bacteria embedded within the biofilm. However the non-bacterial components of the matrix are integral to the structure and function of oral biofilms and provide attractive targets for plaque disruption. Disruption of the extracellular components of the biofilm would physically break-up the plaque and, therefore, disrupt the protection provided by the biofilm. This would facilitate the physical removal of biofilm from hard to reach surfaces. Additionally, bacteria would then be more vulnerable to traditional methods of mechanical removal and chemical antibacterial treatments.

Numerous previous studies have identified enzymes as being potentially valuable for the removal of oral biofilms. However, use of enzymes in oral care formulations presents several challenges. While many enzymes are available, some enzymes and combinations of enzymes are much more effective than others for this use, and it is desirable to identify optimal combinations. Moreover, enzymes are generally commercially available in powdered form, as they are often unstable in liquid form. Using powdered enzymes in a mass manufacturing environment is difficult, as it is hard to measure and control the enzyme amounts accurately and maintain a safe working environment. Moreover, enzymes may present formulation and stability issues when incorporated into oral care products. The relative complexity of dentifrice formulations means that there are a large number of components that have the potential to interfere with the activity and stability of enzymes, and also the enzymes may in some cases degrade other formulation components. Finally, some people may have allergies or other sensitivity to particular enzymes, thus requiring alternatives to existing enzyme formulations.

Therefore, there is a need for stable enzyme preparations that are able to disrupt dental plaque and can be easily incorporated into oral care compositions.

SUMMARY

A large number of different candidate enzymes are evaluated in various combinations for their efficacy and suitability as components of oral care products, and optimal combinations are selected. The invention provides oral care formulations comprising a combination of alkaline protease and a second enzyme selected from cellulase, α-glucanase, and combinations thereof, e.g., oral care products comprising 0.001%-0.1% cellulase/0.002%-0.2% alkaline protease or 0.002%-0.2% α-glucanase/0.002%-0.2% alkaline protease.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

A series of liquid enzymes is assessed for their ability to disrupt dental plaque. The enzymes studied and their targets are as follows:

| Enzyme | Target |
| --- | --- |
| Neutral protease | Proteins |
| Acid protease | Proteins |
| Alkaline protease | Proteins |
| Transglucosidase | Carbohydrates |
| Cellulase | Carbohydrates |
| α-glucanase | Carbohydrates |
| α-amylase | Carbohydrates |
| cutinase | Lipids |

The biofilm matrix is comprised of a variety of extracellular factors that combine to create the sticky structural scaffold of plaque. These extracellular components include: carbohydrates, nucleic acids, lipids, structural proteins, adhesins and signaling molecules. Enzymes are usually specific in their activity and will target only one of these components or, even a small subset of that individual component. Thus, it is expected that combinations of enzymes could potentially target multiple matrix components, allowing for a more complete disruption of the biofilm matrix. The enzymes are initially screened individually against *Actinomyces viscosus* biofilms, then combinations are tested for their ability to disrupt mixed species biofilms.

In one embodiment, the invention provides an oral care composition (Composition 1) comprising an effective amount (e.g., in a concentration effective to disrupt a biofilm) of a combination of alkaline protease and a second enzyme selected from cellulase, α-glucanase, and combinations thereof in an orally acceptable carrier. For example, the invention provides 1.1. Composition 1 wherein the alkaline protease is a serine protease;
1.2. Composition 1 or 1.1 wherein the second enzyme is cellulase;
1.3. Composition 1 or 1.1 wherein the second enzyme is α-glucanase;
1.4. Any of the foregoing compositions comprising 0.002%-0.2% alkaline protease;
1.5. Any of the foregoing compositions comprising 0.001%-0.1% cellulase;
1.6. Any of the foregoing compositions comprising 0.002%-0.2% α-glucanase;
1.7. Any of the foregoing compositions comprising 0.001%-0.1% cellulase and 0.002%-0.2% alkaline protease;
1.8. Any of the foregoing compositions comprising 0.002%-0.2% α-glucanase and 0.002%-0.2% alkaline protease;
1.9. Any of the foregoing compositions wherein the alkaline protease is or is derived from an alkaline protease of bacterial origin, e.g. an alkaline protease from *Bacillus*;

1.10. Any of the foregoing compositions wherein the alkaline protease is a subtilisin;

1.11. Any of the foregoing compositions wherein the alkaline protease is or is derived from an alkaline protease of fungal origin;

1.12. Any of the foregoing compositions wherein the alkaline protease is made by fermentation, e.g., extracted from a bacterial fermentation broth or a fungal fermentation broth.

1.13. Any of the foregoing compositions in a form selected from mouthrinse, toothpaste, tooth gel, tooth powder, non-abrasive gel, mousse, foam, mouth spray, lozenge, oral tablet, dental implement, denture cleaner, and pet oral care product.

1.14. Any of the foregoing compositions wherein the composition is a toothpaste or mouthwash optionally further comprising one or more of one or more of water, abrasives, surfactants, foaming agents, vitamins, polymers, additional enzymes, humectants, thickeners, antimicrobial agents, preservatives, flavorings, colorings and/or combinations thereof;

1.15. Composition 1.10 wherein the composition is a mouthwash;

1.16. Composition 1.10 wherein the composition is toothpaste;

1.17. Any of the preceding compositions wherein the pH is 4.5-6.5, e.g., about 5;

1.18. Any of the preceding compositions further comprising a basic amino acid, e.g., arginine, in free or acid addition salt form, e.g. arginine bicarbonate, arginine phosphate or arginine hydrochloride;

1.19. Any of the preceding compositions further comprising an effective amount of fluoride ion source;

1.20. Any of the preceding compositions comprising the following ingredients by weight, e.g., in the form of a mouthwash:

| Ingredient | Conc. Range % wt/wt |
| --- | --- |
| Water | 50.0-90.0 |
| Humectants, e.g., selected from sorbitol, xylitol, glycerin, propylene glycol and mixtures thereof | 5.0-40.0 |
| Surfactant, e.g., anionic surfactant, e.g., sodium lauryl sulfate, and/or nonionic surfactant, e.g., poloxamer, peglyated castor oil, and/or mixtures thereof | 0.01-10.0 |
| Buffer | 0.01-10.0 |
| Preservatives and stabilizers, e.g. benzoates, chelators such as EDTA, and combinations thereof | 0.01-1.0 |
| Flavor | 0.01-1.0 |
| Polymeric thickener | 0-2 |
| Fluoride ion source | 0-0.3 |
| Arginine (in free or salt form, by weight of the free base) | 0-2.0 |
| Sweetener | 0.001-0.5 |
| Cetylpyridinium chloride | 0-1.0 |
| Cellulase and/or α-Glucanase | 0.001-0.1 cellulase and/or 0.002-0.2 α-glucanase |
| Alkaline Protease | 0.002-0.2 |

The invention further provides methods to (i) inhibit microbial biofilm formation in the oral cavity, (ii) to reduce plaque accumulation, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues; comprising applying to the oral cavity an effective amount of a composition comprising an alkaline protease and a second enzyme selected from cellulase and α-glucanase, e.g., any of Composition 1, et seq.

The invention further provides the use of an alkaline protease and a second enzyme selected from cellulase and α-glucanase in the manufacture of an oral care composition, e.g., according to any of Composition 1, et seq., as well as methods of manufacturing oral care compositions comprising combining an alkaline protease and a second enzyme selected from cellulase and α-glucanase with an orally acceptable carrier, e.g., a toothpaste base or mouthwash base.

The invention further provides a liquid enzyme preconcentrate, e.g., for use in the manufacture of an oral care composition, e.g., according to any of Composition 1, et seq. comprising an alkaline protease and a second enzyme selected from cellulase and α-glucanase.

As used herein, "alkaline protease" refers to a protease that has optimal activity in alkaline conditions, e.g. pH greater than pH 7, e.g., pH 7.5-9.5. The alkaline protease may for example be a natural or modified protein of bacterial origin. In one embodiment, the alkaline protease is a serine protease, for example selected from the group consisting of chymotrypsin-like proteases, subtilisin-like proteases or subtilases, Myxobacter α-lytic proteases, and proteases from *Bacillus*. Protease enzymes are commercially available, for example purified fermentation products, e.g., bacterial or fungal fermentation products, optimally active at high alkaline pH, and stable at a broad range of temperatures, e.g. 25-70° C., such as Properase® enzymes, e.g., Properase 400E (Genencor/DuPont).

In a particular embodiment, the alkaline protease is a subtilase. Subtilases are a family of subtilisin-like serine proteases. Subtilases initiate the nucleophilic attack on the peptide (amide) bond through a serine residue at the active site. They appear to have independently and convergently evolved an Asp/Ser/His catalytic triad, similar to the trypsin serine proteases.

In one particular embodiment the alkaline protease is a subtilisin. Subtilisins (serine endopeptidases) are a class of non-specific proteases (a protein-digesting enzymes) initially obtained from *Bacillus subtilis*. Subtilisins belong to subtilase family. Subtilisins typically have molecular weights of about 20,000 to 45,000 dalton. They can be obtained from soil bacteria, for example, *Bacillus amyloliquefaciens*. Subtilisins are secreted in large amounts from many *Bacillus* species.

As used herein, "cellulase" refers to an enzyme that catalyzes cellulolysis (i.e. the hydrolysis of cellulose). The cellulase may be selected from, e.g., endocellulases, exocellulases, cellobiases, oxidative cellulases and cellulose phosphorylases. In one embodiment, the cellulase is an endocellulase.

As used herein, the term "α-glucanase" refers to an enzyme that catalyzes hydrolysis of 1,3-α-D-glucosidic linkages in a polysaccharide, and so is capable of hydrolyzing insoluble glucan.

pH: The pH of the formulation is preferably weakly acidic, e.g., pH 4.5-6.5, ca. pH 5, particularly where the formulation comprises fluoride, calcium, and/or other ions which are more soluble at lower pH. While an acidic pH is generally less than the optimal pH for alkaline protease activity, we did not find that the lower pH reduced effectiveness the formulations. On the contrary, the alkaline protease is nevertheless found to be surprisingly effective in the lower pH formulations. Without being bound by theory, we believe that the pH in the microenvironment at the site of action may be higher than the pH in the formulation, and that it is this microenvironment pH which is a more relevant factor in determining enzyme activity than the overall pH of the formulation.

Active Agents: The effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Effective ranges for the enzymes in the compositions of the invention are: 0.001%-0.1% cellulase/0.002%-0.2% alkaline protease or 0.002%-0.2% α-glucanase/0.002%-0.2% alkaline protease. Other actives are also provided in effective amounts. Arginine, where present, may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride where present may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial agents in addition to the gallium salt and basic amino acid polymer will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Abrasives: The compositions of the invention, e.g. Composition 1 et seq. may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

Agents to Increase the Amount of Foaming: The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The compositions useful in the invention may contain anionic surfactants, for example
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate,
  ii. higher alkyl sulfates, such as sodium lauryl sulfate,
  iii. higher alkyl-ether sulfates, e.g., of formula CH3(CH2)mCH2(OCH2CH2)nOSO3X, wherein m is 6-16, e.g., 10, n is 1-6, e.g., 2, 3 or 4, and X is Na or K, for example sodium laureth-2 sulfate (CH3(CH2)10CH2(OCH2CH2)2OSO3Na).
  iv. higher alkyl aryl sulfonates such as sodium dodecyl benzene sulfonate (sodium lauryl benzene sulfonate)
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., C6-30 alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular G15 embodiment, the composition of the invention, e.g., Composition 1, et seq., comprises sodium lauryl sulfate.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents: The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Polymers:

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Particularly when noncationic antibacterial agents or antibacterial agents, e.g., triclosan, are included in any of the dentifrice components, there is also preferably included from about 0.05 to about 5% of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference. In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Water: Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants: Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Other optional ingredients: In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional anti-plaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

In one embodiment, the compositions of the invention, e.g., Composition 1, et seq. are mouthwashes, e.g., using base formulations as known in the art, e.g., as described in U.S. Pat. No. 6,692,726, with the improvement that the mouthwashes comprise enzymes as described above for Compositions 1, et seq., e.g., having effective ranges of 0.001%-0.1% cellulase/0.002%-0.2% alkaline protease or 0.002%41.2% α-glucanase/0.002%-0.2% alkaline protease.

In some embodiments, the pH of the mouthwash formulation is about 5, which is substantially lower than the pH normally considered optimal for alkaline protease activity. In some embodiments, a high pH is not necessary for activity of the alkaline protease. In some embodiments, the pH at the site of enzyme action in the biofilm microenvironment is different than the pH of the formulation.

As used throughout, ranges are used as shorthand for describing each and every value that is within the range. Any value within the range can be selected as the terminus of the range. In addition, all references cited herein are hereby incorporated by referenced in their entireties.

In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Enzyme Evaluation Against Single Organism Biofilm

Enzyme systems previously studied presented significant challenges in terms of formulation and stability. Therefore, we examine a series of enzymes produced using bacterial batch fermentation processes. These enzymes provide increased liquid stability and potentially higher activity due to differing targets, as follows:

TABLE 1

Enzymes for evaluation

| Enzyme | Target |
| --- | --- |
| Neutral protease | Proteins |
| Acid protease | Proteins |
| Alkaline protease | Proteins |
| Transglucosidase | Carbohydrates |
| Cellulase | Carbohydrates |
| α-glucanase | Carbohydrates |
| α-amylase | Carbohydrates |
| Cutinase | Lipids |

Enzymes are studied singly and in two- to three-enzyme cocktails in single and mixed species in vitro systems. Additionally, the two most efficacious and readily available cocktails are formulated into mouthrinses and tested in a four-day plaque clinical study.

Bacterial strains and culture conditions: *Actinomyces viscosus* (ATCC#31346) is grown in trypticase soy broth supplemented with 0.6% yeast extract (TSB-YE) at 37° C., static culture. For mixed species assays, the source of bacteria is a continuous culture chemostat inoculated with *A. viscosus, Lactobacillus casei* (ATCC#334), *Streptococcus oralis* (ATCC #35037), *Fusobacterium nucleatum* (ATCC#10953), and *Veilonella parvula* (ATCC#17745). This mixed culture is maintained in a specialized complex medium in a continuous culture chemostat at 37° C.

Saliva coating of hydroxyapatite disks: Growth inhibition and mixed species biofilm inhibition assays are performed using hydroxyapatite (HAP) disks as the surface substrate. Paraffin stimulated saliva is collected from a single donor and centrifuged to pellet the debris. Saliva is then sterilized by incubation under ultraviolet light for 45 minutes. Cleared, sterilized saliva is inoculated into the wells of sterile 24-well culture plates containing HAP disks. Plates are incubated overnight at 4° C. to allow pellicle formation.

Disruption of single species biofilms: Single species biofilms of *A. viscosus* are formed in 96- or 384-well polystyrene culture plates. Bacteria are grown fresh from a frozen stock in 20 ml of TSB-YE at 37° C. overnight. Overnight cultures are diluted to an optical density at 610 nm ($OD_{610}$) of ~0.2 in trypticase soy broth diluted to one-half concentration (0.5×TSB). 100 μl of this dilute culture is added to each well of the appropriate sterile culture plate and plates are incubated overnight at 37° C. Following overnight incubation, supernatants are decanted from the wells leaving behind a robust biofilm on the bottom of each well. Test solutions are added to the first column of each well and two fold serial dilutions are performed in 0.5×TSB across the entire plate. Unless otherwise indicated, plates are incubated for 1 h at 37° C. Following treatment, supernatant are decanted, which removed not only the treatment but any dislodged biofilm. 50 μl of 0.3% Gram's crystal violet is added to each well and allowed to stain for 15 min. Stain is decanted off and wells are washed with a buffer of 10 mM Tris and 1 mM EDTA at a pH of 8.0 and then allowed to dry. Stained plates are read on a Perkin Elmer EnVision microplate reader for absorbance at 590 nm. Absorbances are compared to the absorbance of wells treated with media alone and results are reported as a percent reduction in biofilm formation relative to media control.

The single species biofilm disruption assay is used to screen single enzyme solutions for a number of properties. All eight test enzymes are received as 3-4% solutions in 1% glycerol and all are tested for their ability to disrupt single-species biofilms formed by the oral early colonizer *A. viscosus*. In addition to serving to screen enzymes for potential efficacy, this screen is used to determine dose-response curves for each enzyme alone. This information is used to guide the selection of concentrations for both mixed species assays and for the combination of enzymes into cocktails.

We define the Biofilm Eradication Concentration ($BEC_{50}$) as the lowest concentration at which greater than 50% of the biofilm is disrupted. This allows us to assign a numerical measure of efficacy to each enzyme tested. These values appear in Table 2.

TABLE 2

$BEC_{50}$ for single species *A. viscosus* biofilms

| Enzyme | Target | $BEC_{50}$ (ppm) |
| --- | --- | --- |
| Neutral protease | Proteins | 0.61 |
| Acid protease | Proteins | 39.06 |
| Alkaline protease | Proteins | 0.08 |
| Transglucosidase | Carbohydrates | ** |
| Cellulase | Carbohydrates | 1250 |
| α-glucanase | Carbohydrates | 39.06 |
| α-amylase | Carbohydrates | 5000 |
| cutinase | Lipids | 2500 |

** <50% disruption of biofilm is observed even at the highest concentration (10000 ppm) of enzyme tested.

The neutral and alkaline proteases are the most effective of the enzymes tested at disrupting biofilms formed from an oral early colonizer.

Although single enzymes can be very effective in the disruption of bacterial biofilms, a more comprehensive approach is to use cocktails of multiple different classes of enzymes. The advantage of the cocktail approach is that more than one component of the biofilm matrix is then targeted. Breakdown of multiple components of the matrix ensures a more complete disruption of the biofilm. Therefore, we assess a number of two or three enzyme cocktails. Because the two most effective enzymes are proteases, we include some enzymes in our cocktails that had higher $BEC_{50}$ values. We chose two enzymes that target proteins (neutral protease and alkaline protease), two that target carbohydrates (cellulose and α-glucanase) and one that targets lipids (cutinase). Ten cocktails of two or three enzymes are formulated using these five enzymes in the concentrations and combinations indicated in Table 3. Concentrations for each enzyme are determined based on the $BEC_{50}$.

TABLE 3

Composition of enzyme cocktails

| | 1 | 2 | 3 | 4 | 5 | 6 | 7 | 8 | 9 | 10 |
|---|---|---|---|---|---|---|---|---|---|---|
| Neutral protease (100 ppm) | X | X | X | X | X | | | | | |
| Alkaline protease (100 ppm) | | | | | | X | X | X | X | X |
| α-glucanase (200 ppm) | X | | | X | X | X | | | X | X |
| Cellulase (1000 ppm) | | X | | X | | | X | | X | |
| Cutinase (1000 ppm) | | | X | | X | | | X | | X |

"X" indicates that a given enzyme is present in the cocktail.

These cocktails are first studied in the single-species biofilm disruption assay, as is done for the single enzymes above. Based on the results of this assay, cocktails 2, 3, 7, 8, 9 and 10 are selected for further analysis of their potential efficacy.

All experiments up to this point are performed in media. However, saliva is a complex mix of proteins, salts and other nutrients, as well as digestive enzymes, including proteases. It is possible that one or more of the components of this complex mix could effectively inactivate the enzymes before they could disrupt plaque. To confirm that these enzymes would still be effective in the oral environment, we performed parallel biofilm disruption assays diluting one set of samples in media as had been done previously and diluting one set in whole human saliva. For this assay, the six cocktails identified above are tested in addition to the five individual enzymes making up those cocktails. All six cocktails perform nearly identically whether they are diluted in media or saliva. This indicates that the enzymes are stable in saliva long enough to disrupt the biofilm.

All assays up to this point are performed with a one hour treatment time. However, standard oral care regiments are 30 seconds to 2 minutes long. Therefore, it is important to determine if the enzymes are able to disrupt biofilms within this shorter time scale. The single species biofilm assay is performed with treatment times as short as 30 seconds. In all cases, disruption similar to that seen at 1 hour is observed when incubation times are shortened.

Example 2

Disruption of Mixed Species Biofilms

Although single-species assays are good for rapid screening of a number of options, the actual oral environment is home to over 700 species of bacteria. In order to gain a more complete picture of potential efficacy in the mouth, it is important to study the effect of actives on mixed populations of bacteria. We use a five-species consortium of bacteria as a model for interspecies interactions. This mix of bacteria includes five bacteria that are closely related to the major components of the oral biofilm. The five species include a mix of Gram positive and Gram negative, aerobic and anaerobic, and early and late colonizers. Bacteria used in this model are *A. viscosus, L. casei, S. oxalis, F. nucleatum* and *V. parvula*. This model provides an indication of the efficacy of a particular treatment on a more diverse population than the single-species screen. Most importantly, in this case, it provides a more varied, tenacious biofilm.

Mixed species biofilms are preformed on saliva-coated HAP disks (scHAP). Following saliva coating, disks are inoculated with 1 ml of mixed species culture from the continuous culture described in example 1 diluted to an $OD_{610}$ of ~0.2 in 0.5×TSB. Plates are incubated for 24 h at 37° C. to allow biofilms to form. Disks containing pre-formed biofilms are transferred to a fresh 24-well culture plate and 0.5 ml of test solution is added to each disk. Plates are incubated for 1 h at 37° C. with gentle agitation. Following treatment, disks are removed to a plate containing fresh 0.5×TSB to rinse off the treatment solution and any loosened biofilm. Disks are then transferred to 15 ml polystyrene tubes containing 1 ml of a 0.25% trypsin solution. Disks are incubated at 37° C. with shaking for 45 min. Tubes are briefly vortexed to resuspend the bacteria and supernatants are transferred to a fresh 24-well plate. Plates are sonicated for 2 min to pellet any residual HAP and supernatants are removed to fresh plates so that absorbance could be read at 610 nm. All samples are tested in triplicate and the average of the three wells determined. Results are reported as a percent reduction in biofilm formation relative to a disks treated with media alone.

Previous studies using this five-species mix of bacteria have focused on the ability of compounds to inhibit formation of biofilms. Adaptations had to be made to look at the disruption of existing biofilms. Mixed species biofilms are pre-formed on saliva-coated hydroxyapatite disks for 48 h. Disks are removed to fresh media and treated for 1 h with 1 ml of the test solution under gentle agitation. This agitation allowed for the mechanical removal of biofilm that is enzymatically loosened from the HAP disk. Following treatment, remaining biofilm is removed from the disk by treatment with trypsin and quanitified. Results are represented as a percent reduction in biofilm relative to a control incubated in media alone.

Cocktails 2, 7, and 9, and the relevant single enzymes are tested for disruption of pre-formed mixed species biofilms by single enzymes and two enzyme cocktails. Results are given as the percent reduction in biofilm relative to disks incubated in media alone. A combination of glucoamylase (0.044%) and a papain (0.226%) having optimal activity at a pH of 5-7, which prior work has shown to be effective is used as a positive control.

TABLE 4

| Mixed species biofilm disruption relative to media (%) | |
|---|---|
| Media | 0 |
| Glucoamylase/papain (positive control) | 23 |
| Neutral protease | 19 |
| Alkaline protease | 11 |
| Cellulase | 16 |
| Cocktail 2 | 17 |
| Cocktail 7 | 39 |
| Cocktail 9 | 22 |

Cocktail 7, which contains 100 ppm alkaline protease and 200 ppm cellulase greatly outperforms any of the single enzymes or cocktails, including the positive control of glucoamylase and papain.

Example 3

Formulation

The relative complexity of dentifrice formulations means that there are a large number of components that have the potential to interfere with the activity and stability of enzymes. This, combined with the fact that the enzymes are already known to be stable in simple liquid solutions, lead us to attempt to formulate the enzymes into a mouthwash.

Although the alkaline protease/cellulase cocktail greatly outperformed the other cocktails tested, concerns over the use of cellulase prompted us to explore the formulation of an alternative enzyme rinse for further study. Cellulase is an enzyme that hydrolyzes the 1,4-β-D-glycosidic linkages in cellulose molecules. Cellulose gums are commonly used as thickeners in toothpaste formulations and sometimes in mouthwashes. The presence of even minute amounts of cellulase in the vicinity of dentifrice making equipment could lead to severe thinning, or even liquification, of the dentifrices. We therefore chose a second cocktail for evaluation, which would be suitable for eventual incorporation into a formulation containing cellulose gums, if that was desired. Based on a combination of previous in vitro studies and practical considerations, we chose to make the following three enzyme mouthwashes: 0.1% cellulose+0.2% alkaline protease; 0.2% α-glucanase+0.2% alkaline protease; and 0.044% glucoamylase+0.226% papain as a positive control:

TABLE 5

Test formulations

| Ingredient | % w/w | | |
|---|---|---|---|
| Demineralized Water | 36.68 | 6.95 | 6.95 |
| Sorbitol (70% solution) | 22.28 | 22.28 | 22.28 |
| Glycerin | 22.96 | 22.96 | 22.96 |
| Propylene Glycol | 16.07 | 16.07 | 16.07 |
| Sodium Saccharin | 0.05 | 0.05 | 0.05 |
| Sodium Benzoate | 0.25 | 0.25 | 0.25 |
| Benzoic Acid | 0.12 | 0.12 | 0.12 |
| Cetylpyridinium Chloride | 0.015 | 0.015 | 0.015 |
| Disodium EDTA | 0.006 | 0.006 | 0.006 |
| Calcium Chloride | 0.1 | 0.1 | 0.1 |
| Poloxamer 407 | 0.5 | 0.5 | 0.5 |
| Poloxamer 338 | 0.5 | 0.5 | 0.5 |
| PEG-40 Castor Oil | 0.1 | 0.1 | 0.1 |
| Flavor | 0.1 | 0.1 | 0.1 |
| Cellulase (1% solution) | — | — | 20 |
| α-Glucanase (1% solution) | — | 20 | — |
| Alkaline Protease (1% solution) | — | 10 | 10 |
| Glucoamylase | 0.044 | — | — |
| Papain | 0.226 | — | — |

Following formulation, the first step is to confirm that the enzymes are stable in the formulations and retain their biofilm disruptive activity. The ingredients in the mouthwash base have a considerable effect on biofilm removal, even without the addition of enzymes. Therefore, an enzyme-free formulation as placebo control is tested as well.

All three mouthrinses demonstrate a high degree of biofilm removal relative to that observed for the placebo. This indicated that the enzyme cocktails remained highly active within the matrix of a mouthwash formula. We also are able to confirm that the alkaline protease/α-glucanase enzyme cocktail is effective at single-species biofilm removal. This assay is repeated on mouthrinse formulas following up to three months incubation at room temperature. Similar biofilm disruptive activity is maintained over this period of time, indicating that the enzymes are relatively stable in this mouthwash formula.

It is also important to demonstrate that these mouthwashes are active against mixed species biofilms. Due to the high viscosity of the enzyme mouthwash base formulation, there is a very high degree of biofilm removal due to the placebo mouthwash alone. Therefore, reductions in biofilm relative to the placebo are considerably lower than is observed for the unformulated enzyme cocktails. However, the same performance trends are observed as previously seen in this experiment.

TABLE 6

Disruption of mixed species biofilms by enzyme mouthwashes,
as a percent reduction in biofilm relative to the placebo
(levels of biofilm reduction lower than for neat solutions
due to the high placebo effect observed in this assay)

| | |
|---|---|
| Enzyme-free placebo | 0 |
| Glucoamylase + papain (positive control) | 11 |
| Alkaline protease/cellulase | 36 |
| Alkaline protease/alpha-glucanase | 15 |

These in vitro studies demonstrate that both prototype enzyme mouthwashes perform at or above the level of the benchmark glucoamylase-papain enzyme cocktail, and are much better than the enzyme-free control mouthwash. A number of previous studies have demonstrated good clinical efficacy of glucoamylase-papain dentifrices, so good performance in comparison with this positive control is encouraging.

The invention claimed is:
1. An oral care composition consisting of
   (a) 0.002% -0.2% by weight of a serine protease and 0.001% -0.1% by weight of a cellulase, and
   (b) one or more of a fluoride ion source, a basic amino acid, water, abrasives, surfactants, foaming agents, vitamins, polymeric thickeners, humectants, antimicrobial agents, preservatives, flavorings, and colorings.
2. The composition of claim 1 wherein the serine protease is a subtilisin.
3. The composition of claim 1 wherein the serine protease is of fungal or bacterial origin.
4. The composition of claim 1 in a form selected from a mouthrinse, a toothpaste, a tooth gel, a tooth powder, a non-abrasive gel, a mousse, a foam, a mouth spray, a lozenge, an oral tablet, a denture cleaner, and a pet oral care product.
5. The composition of claim 1 wherein the composition is selected from a toothpaste and a mouthwash.
6. The composition of claim 1 wherein the pH of the composition is 4.5 to 6.5.
7. The composition of claim 1 wherein the basic amino acid is in free or acid addition salt form.
8. The composition of claim 1 wherein the surfactant is a mixture consisting of sodium lauryl sulfate, poloxamer, and pegylated castor oil.
9. The composition of claim 1 that is a mouthwash consisting of the following ingredients by weight:

| Ingredient | Concentration Range % wt/wt |
|---|---|
| Water | 50-90 |
| Humectant | 5-40 |
| Surfactant | 0.01-10 |
| Buffer | 0.01-10 |
| Preservatives and stabilizers | 0.01-10 |
| Flavor | 0.01-10 |
| Polymeric thickener | 0-2 |
| Fluoride ion source | 0-0.3 |
| Arginine (in free or salt form, by weight of the free base) | 0-2 |
| Sweetener | 0.001-0.5 |
| Cetylpyridinium chloride | 0-1 |
| Cellulase and/or α-Glucanase | 0.002-0.2 |
| Alkaline Protease | 0.002-0.2 |

10. A method to (i) inhibit microbial biofilm formation in the oral cavity, (ii) to reduce plaque accumulation, (iii) reduce or inhibit gingivitis, (iv) reduce or inhibit formation of dental caries, (v) clean the teeth and oral cavity, and/or (vi) promote whole body health; comprising applying to the oral cavity an effective amount of a composition of claim 1.

* * * * *